United States Patent [19]
Zahn et al.

[11] Patent Number: 5,654,471
[45] Date of Patent: Aug. 5, 1997

[54] PROCESS FOR THE PREPARATION OF 4-HYDROXYPHENYL BENZOATE DERIVATIVES

[75] Inventors: Ingo Zahn, Emmerting; Norman Haeberle, München; Peter Weitzel, Reischach, all of Germany

[73] Assignee: Consortium für Elektrochemische Industrie GmbH, München, Germany

[21] Appl. No.: 552,238

[22] Filed: Nov. 2, 1995

[30] Foreign Application Priority Data

Dec. 1, 1994 [DE] Germany ............. 44 42 831.6

[51] Int. Cl.[6] ............................. C07C 69/76
[52] U.S. Cl. ............................. 560/109; 560/73
[58] Field of Search ................ 560/109, 73

[56] References Cited

U.S. PATENT DOCUMENTS

| | | |
|---|---|---|
| 3,594,408 | 7/1971 | Hosler ............. 560/109 |
| 4,855,484 | 8/1989 | Müller et al. . |
| 5,211,877 | 5/1993 | Andrejewski et al. . |

FOREIGN PATENT DOCUMENTS 0252357  1/1988  European Pat. Off. .

*Primary Examiner*—Paul J. Killos
*Attorney, Agent, or Firm*—Collard & Roe, P.C.

[57] ABSTRACT

4-Hydroxyphenyl benzoate derivatives of the general formula 1:

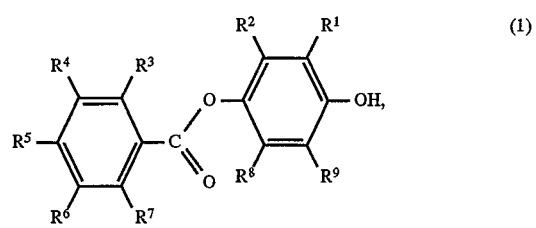

are prepared by cleaving 1,4-bis(benzoyl)hydroquinone derivatives of the general formula 2:

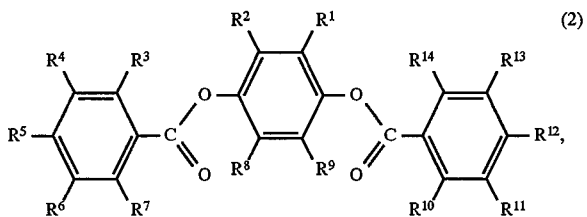

with alkali metal alkanolates, in which in the general formulae 1 and 2 $R^1$ to $R^{14}$ are as defined in claim 1.

4 Claims, No Drawings

PROCESS FOR THE PREPARATION OF 4-HYDROXYPHENYL BENZOATE DERIVATIVES

BACKGROUND OF THE INVENTION

1. Field of the Invention

The present invention relates to a process for the preparation of 4-hydroxyphenyl benzoate derivatives.

2. The Prior Art

4-Hydroxyphenyl benzoate derivatives are important organic intermediates which have hitherto been difficult to prepare. For example, 4-hydroxyphenyl benzoate derivatives in which a radical having an alkenyl or alkynyl group is located in the 1-position of the benzoic acid ring are used for the preparation of liquid-crystalline siloxane-containing side-chain polymers.

The main problem associated with the synthesis of 4-hydroxyphenyl benzoate derivatives consists in coupling bifunctional hydroquinone derivative with benzoic acid compounds on only one side. In the preparative process known from U.S. Pat. No. 5,211,877, allyloxybenzoyl chloride is reacted with a very large excess of hydroquinone. The disadvantage of this method is that the excess hydroquinone has to be laboriously separated off after the reaction, leading to a poor space-time yield of 4-hydroxyphenyl allyloxybenzoate.

SUMMARY OF THE INVENTION

It is an object of the present invention to provide an improved process for the preparation of 4-hydroxyphenyl benzoate derivatives.

The present invention relates to a process for the preparation of 4-hydroxyphenyl benzoate derivatives of the general formula 1:

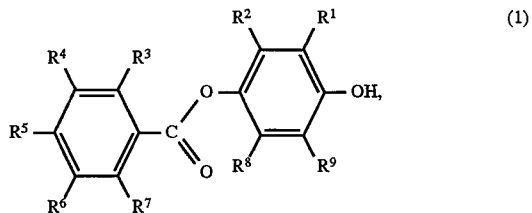

wherein 1,4-bis(benzoyl)hydroquinone derivatives of the general formula 2:

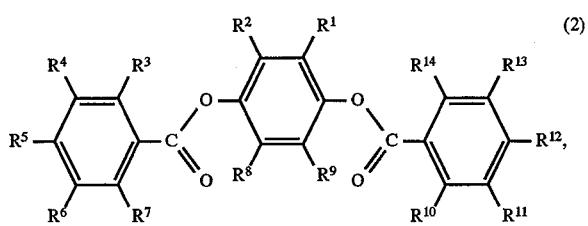

are reacted with alkali metal alkanolates,
in which in general formulae 1 and 2:
$R^1, R^2, R^3, R^4, R^6, R^7, R^8, R^9, R^{10}, R^{11}, R^{13}$ and $R^{14}$ are identical or different radicals selected from hydrogen atoms, halogen atoms, nitro and cyano groups and $C_1$- to $C_4$-alkoxy, $C_1$- to $C_6$-alkyl, carboxy ($C_1$- to $C_4$-alkyl) and tri($C_1$- to $C_4$-alkyl)-siloxy radicals and $R^5$ and $R^{12}$ are identical or different radicals selected from hydrogen atoms and $C_1$- to $C_{20}$-alkyl, $C_2$- to $C_{20}$-alkenyl and $C_2$- to $C_{20}$-alkynyl radicals, it being possible in each case for one or more non-adjacent methylene units to be replaced with oxygen atoms.

In this novel general synthesis procedure, the 1,4-bis(benzoyl)hydroquinone derivatives of the general formula 2 are cleaved, in a clean reaction and with a very good yield, to give the corresponding 4-hydroxy-phenyl benzoate derivatives of the general formula 1 and the benzoic acid ester derivatives of the general formula 3:

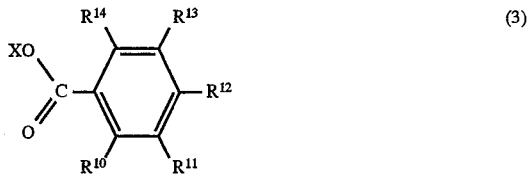

wherein
X is an alkyl radical and
$R^{10}, R^{11}, R^{12}, R^{13}$, and $R^{14}$ are as defined for the general formulae 1 and 2.

The benzoic acid ester derivatives of the general formula 3 are also often required as intermediates in organic chemistry, for example for the synthesis of other mesogens which can be incorporated into liquid-crystalline silicones, and thus are desirable coupling products.

Examples of the $C_1$- to $C_6$-alkyl radicals $R^1, R^2, R^3, R^4, R^6, R^7, R^8, R^9, R^{10}, R^{13}$ and $R^{14}$ are the methyl, ethyl, n-propyl, isopropyl, n-butyl, isobutyl, tert-butyl, n-pentyl, isopentyl, neopentyl, tert-pentyl and cyclopentyl radicals, and hexyl radicals such as the n-hexyl radical and the cyclohexyl radical.

Examples of the $C_1$- to $C_4$-alkyl radicals forming part of the $C_1$- to $C_4$-alkoxy, carboxy($C_1$- to $C_4$-alkyl) and tri($C_1$- to $C_4$-alkyl)siloxy radicals $R^1, R^2, R^3, R^4, R^6, R^7, R^8, R^9, R^{10}, R^{11}, R^{13}$ and $R^{14}$ are the $C_1$- to $C_4$-alkyl radicals listed above.

Suitable halogen atoms are preferably fluorine, chlorine and bromine.

Examples of $C_1$- to $C_{20}$-alkyl radicals $R^5$ and $R^{12}$ are the $C_1$- to $C_6$-alkyl radicals listed above, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, octadecyl radicals such as the n-octadecyl radical, and cycloalkyl radicals such as cyclopentyl, cyclohexyl, cycloheptyl and methylcyclohexyl radicals.

Examples of $C_2$- to $C_{20}$-alkenyl radicals $R^5$ and $R^{12}$ are vinyl, allyl and prop-1-enyl radicals, butenyl radicals such as the n-but-1-enyl, n-but-2-enyl, and buta-1,3-dienyl radicals, pentenyl radicals such as the n-pent-4-enyl and isoprenyl radicals, hexenyl radicals such as the n-hex-5-enyl radical, heptenyl radicals, octenyl radicals, nonenyl radicals, decenyl radicals, dodecenyl radicals and octadecenyl radicals, and cycloalkenyl radicals such as cyclopentenyl, cyclohexenyl, cyclo-heptenyl and methylcyclohexenyl radicals.

Examples of $C_2$- to $C_{20}$-alkynyl radicals $R^5$ and $R^{12}$ are ethynyl, prop-1-ynyl and propargyl radicals, butynyl radicals such as the but-1-ynyl, but-2-ynyl and buta-diynyl radicals, pentynyl radicals such as the n- pent-4-ynyl radical, hexynyl radicals such as the n- hex-5-ynyl and hexa-1,3,5-triynyl radicals, heptynyl radicals, octynyl radicals, nonynyl radicals, decynyl radicals, dodecynyl radicals and octadecynyl radicals.

Examples of $C_1$- to $C_{20}$-alkyl, $C_2$- to $C_{20}$-alkenyl and $C_2$- to $C_{20}$-alkynyl radicals $R^5$ and $R^{12}$ in which in each case one or more non-adjacent methylene units have been replaced with oxygen atoms are the n- decyloxy, allyloxy, n-pent-4-enyloxy and n-hex-5-ynyl radicals.

Preferred radicals $R^5$ and $R^{12}$ are the $C_1$- to $C_{15}$-alkyloxy, $C_2$- to $C_{15}$-alkenyloxy and $C_2$- to $C_{15}$-alkynyloxy radicals, especially the linear radicals. The linear alkenyloxy and alkynyloxy radicals which have only one alkenyl or alkynyl group in the end position are preferred.

In particular, 1,4-bis(benzoyl)hydroquinone derivatives of the general formula 2 in which $R^5$ and $R^{12}$ are identical are used in the process.

The alkali metal alkanolates used are preferably the compounds of the general formula 4:

$$MOX \qquad (4),$$

in which

M is a lithium, sodium or potassium atom and

X is a $C_1$- to $C_6$-alkyl radical.

Examples of the $C_1$- to $C_6$-alkyl radicals X are listed above.

In the reaction, the chosen ratio of 1,4-bis(benzoyl)-hydroquinone derivative of the general formula 2 to alkali metal alkanolate is preferably 1.0 to 2.0 mol, especially 1.1 to 1.7 mol.

The reaction is preferably carried out at temperatures of 0° C. to 120° C., especially 30° C. to 90° C. The pressure is preferably 0.05–1 MPa, especially 0.09–0.2 MPa.

The cleavage reaction is preferably carried out in solvents. If solvents are used, they are preferably solvents or solvent mixtures which are substantially inert under the reaction conditions, especially those with a boiling point or boiling point range of up to 120° C. at 0.1 MPa. Examples of such solvents are ethers such as dioxane, tetrahydrofuran, diethyl ether, methyl tert-butyl ether and diethylene glycol dimethyl ether; chlorinated hydrocarbons such as dichloromethane, chloroform, carbon tetrachloride, 1,2-dichloroethane and trichloroethylene; hydrocarbons such as pentane, n-hexane, mixtures of hexane isomers, heptane, octane, solvent naphtha, petroleum ether, benzene, toluene and xylenes; ketones such as acetone, methyl ethyl ketone and methyl isobutyl ketone; esters such as ethyl acetate, methyl acetate, n-butyl acetate and ethyl formate; carbon disulfide and nitrobenzene, or mixtures of these solvents. The term solvent does not mean that all the reactants must dissolve therein. The reaction can also be carried out in a suspension or emulsion of one or more reactants. The reaction can also be carried out in a solvent mixture with a miscibility gap, at least one reactant being soluble in each of the mixed phases.

The solvents used are especially the aprotic solvents such as the cyclic ethers and acyclic ethers.

Other objects and features of the present invention will become apparent from the following Example, which discloses the embodiments of the present invention. It should be understood, however, that the Example is designed for the purpose of illustration only and not as a definition of the limits of the invention.

The following Example serves to illustrate the invention in greater detail.

EXAMPLE

The following are used:

222 g (0.516 mol) of 1,4-bis(4-allyloxybenzoyl) hydroquinone (CAS no. 85234-29-3)

29.55 g of sodium methylate 500 ml of THF, 400 ml of petroleum ether (40°–60° C.)

200 ml of dilute sulfuric acid, and $Na_2SO_4$ for drying.

The 1,4-bis(4-allyloxybenzoyl)hydroquinone is suspended in the THF. The sodium methylate is then added, with stirring. The mixture is subsequently refluxed for a further two and a half hours and the dilute sulfuric acid is then added to the product. When stirring has ended, two phases separate. The lower, aqueous phase is discarded and the organic phase is washed with water. The product solution is dried over $Na_2SO_4$ and then evaporated. Monoallyloxy-benzoic acid hydroquinone crystallizes out as the oil cools. The product is then suspended in the 400 ml of petroleum ether and filtered off with suction. The methyl allyloxybenzoate is in the petroleum ether phase. Yield: 90% of theory.

While several embodiments of the present invention have been shown and described, it is to be understood that many changes and modifications may be made thereunto without departing from the spirit and scope of the invention as defined in the appended claims.

What is claimed is:

1. A process for the preparation of 4-hydroxyphenyl benzoate derivatives of the general formula 1:

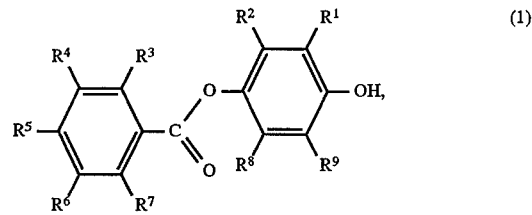

wherein 1,4-bis(benzoyl)hydroquinone derivatives of the general formula 2:

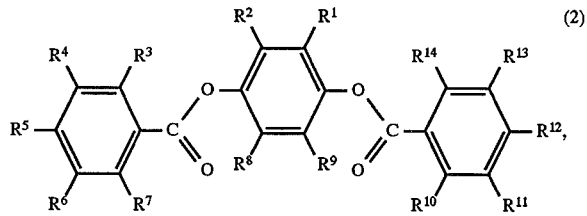

are reacted with alkali metal alkanolates, in which in general formulae 1 and 2:

$R^1$, $R^2$, $R^3$, $R^4$, $R^6$, $R^7$, $R^8$, $R^9$, $R^{10}$, $R^{11}$, $R^{13}$ and $R^{14}$ are identical or different radicals selected from the group consisting of hydrogen atoms, halogen atoms, nitro groups and cyano groups and $C_1$- to $C_4$-alkoxy, $C_1$- to $C_6$-alkyl, carboxy ($C_1$- to $C_4$-alkyl) and tri($C_1$- to $C_4$-alkyl)-siloxy radicals and $R^5$ and $R^{12}$ are identical or different radicals selected from the group consisting of hydrogen atoms and $C_1$- to $C_{20}$-alkyl, $C_2$- to $C_{20}$-alkenyl and $C_2$- to $C_{20}$-alkynyl radicals, it being possible in each case for one or more non-adjacent methylene units to be replaced with oxygen atoms;

wherein the ratio of the 1,4-bis(benzoyl)-hydroquinone derivative to the alkali metal alkanolate is from 1.0 to 2.0 mol; and wherein the reaction is carried out at a temperature of 0° to 120° C., and the pressure is 0.05–1 MPa.

2. The process as claimed in claim 1, wherein $R^5$ and $R^{12}$ are $C_1$- to $C_{15}$-alkoxy, $C_2$- to $C_{15}$-alkenyloxy or $C_2$- to $C_{15}$-alkynyloxy radicals.

3. The process as claimed in claim 1, wherein 1,4-bis (benzoyl)hydroquinone derivatives of the general formula 2 are used in which $R^5$ and $R^{12}$ are identical.

4. The process as claimed in claim 1, wherein the alkali metal alkanolates used are the compounds of the general formula 4:

$$MOX \qquad (4),$$

wherein

M is a lithium, sodium or potassium atom and

X is a $C_1$- to $C_6$-alkyl radical.

* * * * *